Figure 1:
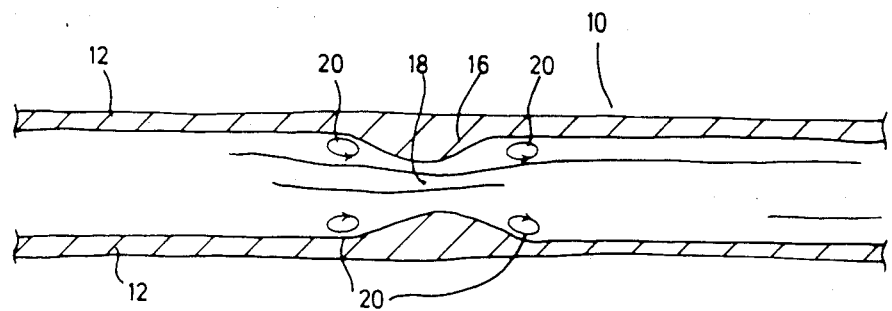

United States Patent [19]

Fenster et al.

[11] Patent Number: 4,669,105
[45] Date of Patent: May 26, 1987

[54] SYSTEM FOR QUANTITATIVE ARTERIOGRAPHY

[76] Inventors: Aaron Fenster; Barry B. Hobbs; Ian A. Cunningham, all of Radiological Research Laboratories, Medical Sciences Building, University of Toronto, 1 King'College Cir., Toronto, Ontario, Canada, M5S 1A8

[21] Appl. No.: 614,599

[22] Filed: May 29, 1984

[51] Int. Cl.⁴ .......................... H05G 1/64; H04N 5/32
[52] U.S. Cl. ...................................... 378/146; 378/99; 358/111; 128/653
[58] Field of Search .................. 378/146, 99; 358/111, 358/146; 128/653, 659

[56] References Cited

U.S. PATENT DOCUMENTS

| | | | |
|---|---|---|---|
| 4,111,191 | 9/1978 | Shaw | 128/659 |
| 4,399,457 | 8/1983 | Riederer et al. | 378/99 |
| 4,404,591 | 9/1983 | Bonar | 378/146 |
| 4,466,113 | 8/1984 | Strecker | 378/146 |
| 4,479,231 | 10/1984 | Haendle et al. | 358/111 |

Primary Examiner—Craig E. Church
Assistant Examiner—Charles F. Wieland

[57] ABSTRACT

Apparatus for the generation of an image of a blood vessel comprises an x-ray source to irradiate the vessel. X-ray image collection means receive the x-ray image of the vessel and conversion means convert the x-ray image into a visible image of the vessel. A collimator selects an elongate field of illumination representative of a section of the blood vessel. A light detecting array receives the field of illumination and has a plurality of discreet detectors spaced along the axis of the elongated field. Each detector has a length at least equal to the width f the elongate field produces a signal upon impingement by the elongate field. The array is scanned sequentially to output the signals in series. The signals are then displayed as one line of a video display.

15 Claims, 10 Drawing Figures

SYSTEM FOR QUANTITATIVE ARTERIOGRAPHY

The present invention relates to x-ray imaging apparatus that is useful for angiographic imaging and research.

The development of digital X-ray imaging techniques has allowed for the rapid growth of specialised procedures for studying cardiovascular disease. Digital Substraction Angiography (DSA) is one such technique that is used to image vessels that have been contrast enhanced by the injection of a radio-opaque dye. Many commercial DSA systems presently available provide X-ray images through the use of an X-ray image intensifier optically coupled to a video camera. The video signal is digitized and stored in a computer for display and processing. Images of the contrasted vessels are produced by subtracting post-injection from pre-injection images. This removes structure common to both and leaves the contrast enhanced structures.

In an angiographic examination, the radiologist may be looking for the presence and location of arterial stenoses. The appearance of these vessel narrowings in the X-ray image will depend on their geometric orientation with respect to the direction of the X-ray view. For instance a deposit on a surface tangential to the propagation direction of the X-raybeam will appear as a vessel narrowing and may be relatively easy to see. A deposit on a surface perpendicular to the beam direction will only appear as a small contrast change that may be obscured by image noise and be very difficult to detect. The detectability of the stenosis in any one single view can be increased if the image noise can be reduced. However, video cameras are inherently noisy and therefore it is difficult to accurately detect the presence of low contrast detail.

It is therefore an object of the present invention to obviate or mitigate the above disadvantages.

According therefore to the present invention there is provided: Apparatus for generating an image of a blood vessel comprising an x-ray source to irradiate said blood vessel, x-ray image collection means to receive an x-ray image including said blood vessel, conversion means to convert said x-ray image into a visible image, collimating means to select a discreet portion of said visible image and produce an elongate field of illumination representative of the blood vessel, a light detection arrangement to receive said elongate field of illumination and having a plurality of discrete detectors spaced along the axis of the elongate field each having a length at least equal to the width of the elongated field to produce a signal upon impingement by said elongate field and scanning means to scan sequentially said detectors and output said signals in series.

By imaging small regions of interest and using a linear array of photodiodes as a replacement for the video camera, it is possible to reduce the noise in the system and so improve the detectability of arterial stenoses regardless of their geometrical orientation. This has the advantage that low contrast lesions can be detected and the potential hazard to a patient from adverse reactions to the radio-opaque dye that is injected to give contrast to the arteries is decreased as lower concentrations of the dye can be used.

Figure 2:
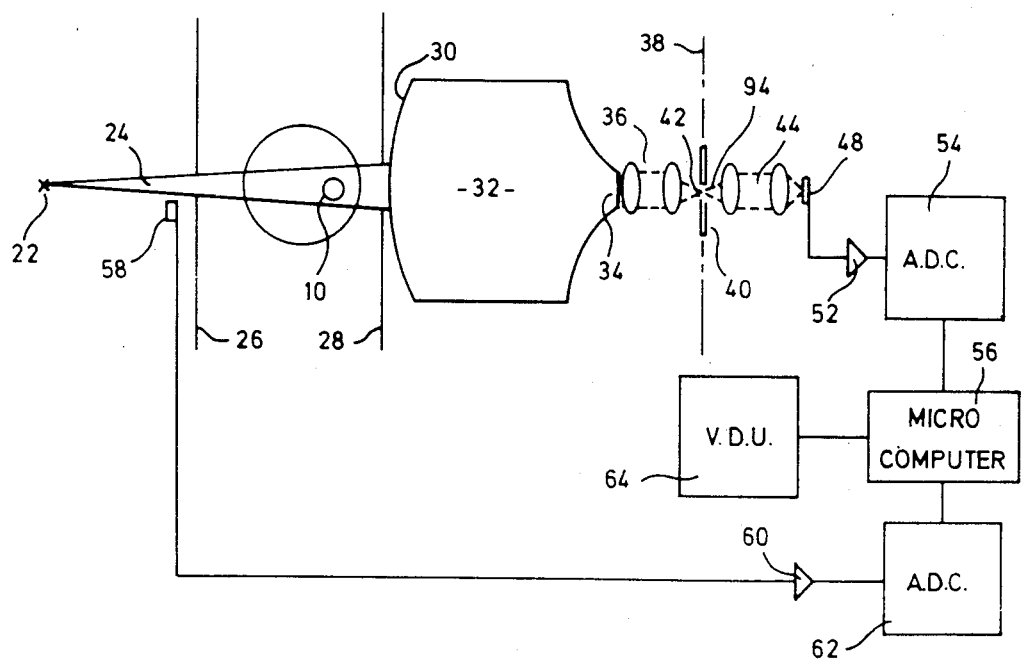
Figure 3:
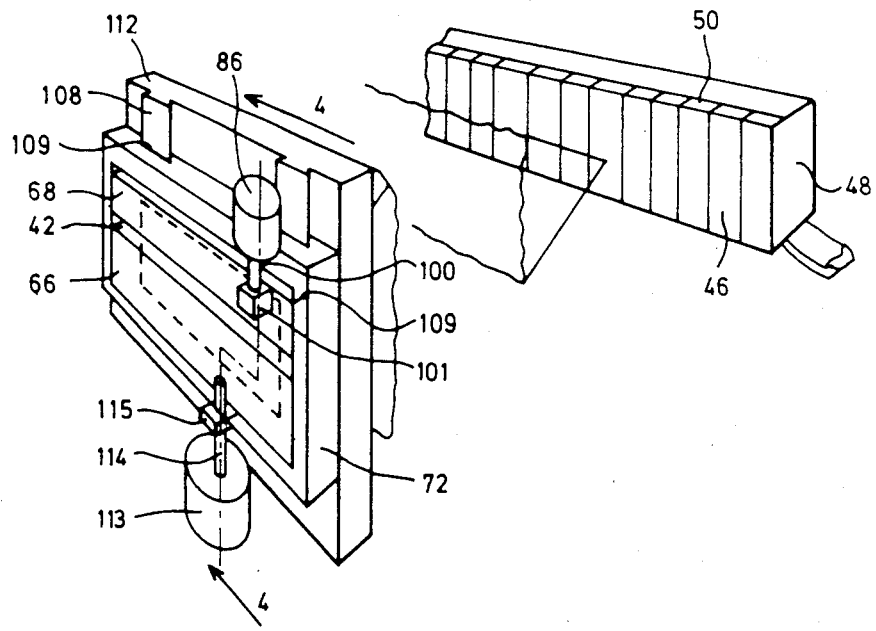
Figure 4:
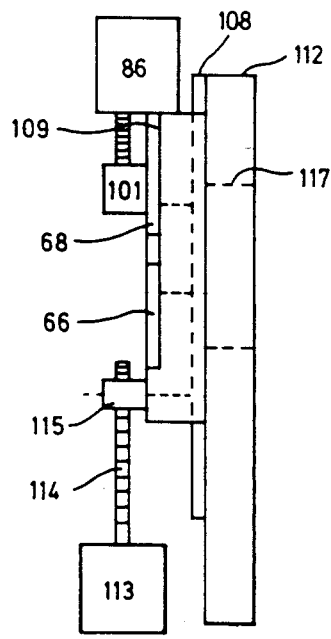
Figure 5:
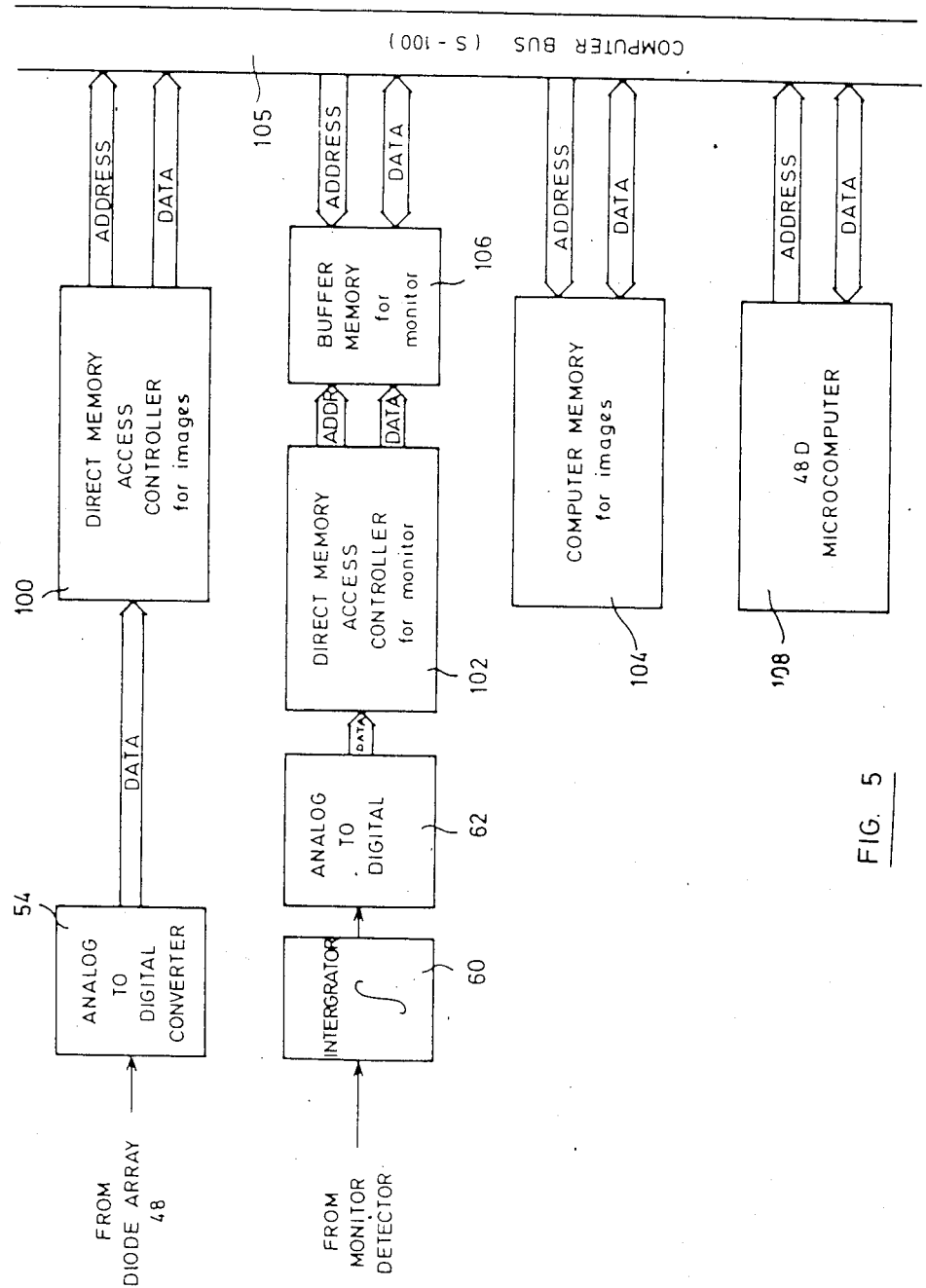
Figure 6:
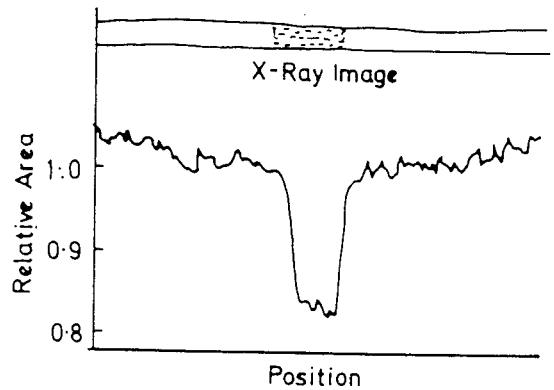
Figure 7:
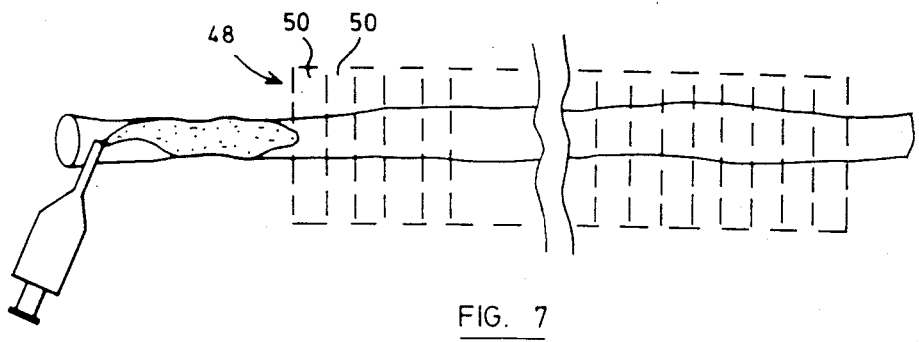
Figure 8:
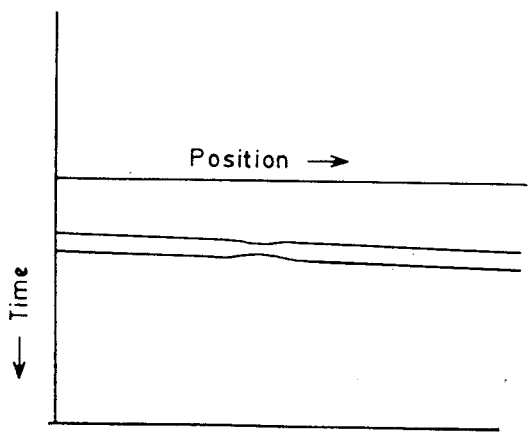
Figure 9:
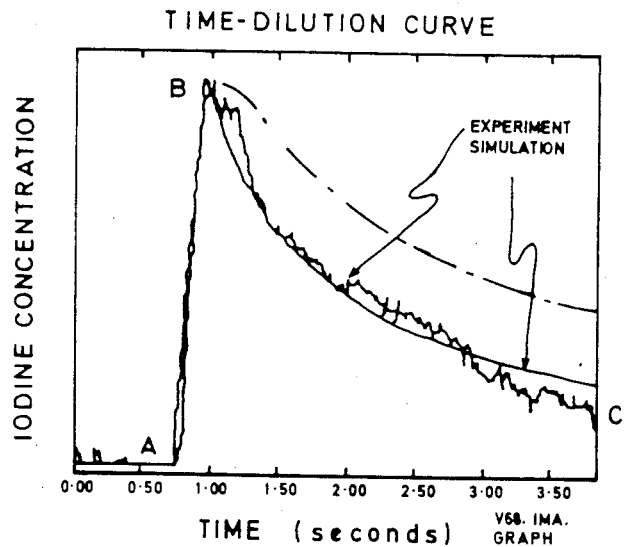
Figure 10:
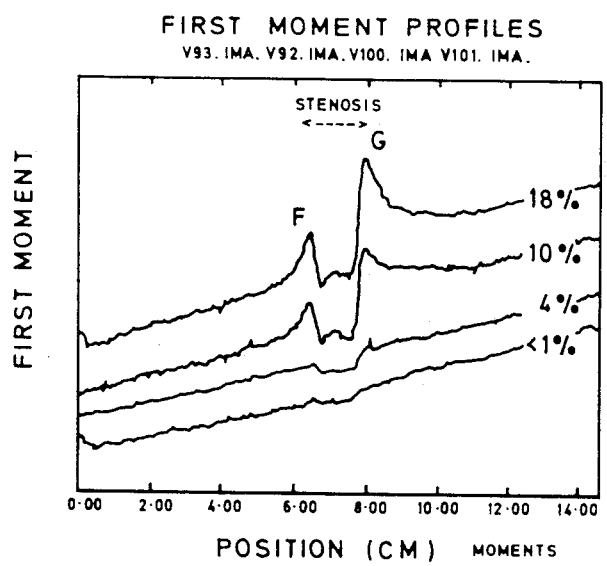

Embodiments of the present invention will now be described by way of example only with reference to the accompanying drawings in which:

FIG. 1 is a schematic representation of a stenosis in a blood vessel,

FIG. 2 is a schematic view of apparatus for detecting the presence of the stenosis shown in FIG. 1, FIG. 3 is a perspective view of a portion of the apparatus shown in FIG. 2, FIG. 4 is a view on the line 4—4 of FIG. 3 showing in further detail a portion of the apparatus shown in FIG. 2, FIG. 5 is a block diagram of the computer interface for processing the data obtained from the apparatus of FIG. 2, FIG. 6 is an illustration of the representative results obtained through the apparatus of FIG. 2, FIG. 7 is a schematic representation of the arrangement of the apparatus in FIG. 2 to detect stenosis by a different procedure using the apparatus shown in FIG. 2, FIG. 8 is a representation of the results obtained from the apparatus of FIG. 2 using the procedure shown in FIG. 7, FIG. 9 is a representation of experimental results obtained by manipulating the data represented in FIG. 8 to provide further information relating to the stenosis shown in FIG. 1, FIG. 10 is a representation of the further results obtained from the procedure shown in FIG. 6 by processing the results obtained through a different procedure.

Referring now to the drawings there is shown in FIG. 1 a representative of an artery 10 having a wall 12 defining an interior passage 14 through which blood can flow. The wall 12 has local thickening indicated at 16 that constitute a stenosis 18 and restricts the flow of blood in the passage 14. The stenosis 18 may be sufficient to cause flow separation to either side of the thickening 16 as indicated by the zones 20. The presence of the stenosis 18 may constitute a significant risk to the patient under observation and it is therefore desirable to identify the stenosis 18 and to obtain as much information as possible about the stenosis and its effect on the flow of blood through the passage 14.

Apparatus for imaging the stenosis and quantifying its parameters is shown in FIG. 2. The apparatus comprises an X-ray source 22 that provides a beam of X-rays 24 to irradiate the artery 10. The artery 10 is located between a pair of lead collimators 26, 28 respectively. The collimator 26 controls the shape of the beam 24 that impinges upon the artery 10 and the collimator 28 controls the resultant image beam and inhibits spurious X-rays being introduced due to scatter. The beam 24 after passing through the collimator 28 impinges upon an input face 30 of a image intensifier 32. The collimator 28 controls the area exposed on the input face 30 and so reduces background caused by scatter in the intensifier. The image intensifier used in prototype apparatus is a Philips XG2010 9"/5" CSI intensifier that converts the X-ray image that impinges on the input face 30 into a visible image appearing on the output face 34.

The visible image on the output face 34 is processed by an optical system 36 that focuses the image at a focused image plane indicated by the line 38. Located in the image plane 38 is a collimator 40 having a slit 42 extending transverse to the optical axis of the optical system 36. The image that passes through the slit 42 is processed by a second optical system 44 and focused onto the input face 46 of a photodiode array 48.

The diode array comprises a plurality of discrete elements 50 that are spaced apart along an axis that is generally parallel to the axis of the slit 42. The element 50 converts the visible image that impinges on the input face 46 into an electrical signal and each of the elements is scanned sequentially to provide a pulse train that is fed to an amplifier 52. The amplified signal is processed by an analog to digital converter (ADC) 54 so that a digital signal corresponding to the output of each of the elements 50 is available for storage in a microcomputer 56.

An X-ray monitor 58 is provided between the X-ray source 22 and the lead collimator 26 to monitor variations in the intensity of the source 22. Signals from the monitor 58 are fed through an integrating amplifier 60 into an analog to digital converter 62 where they are digitized and provided to the microcomputer 56. The microcomputer 56 operates upon the signals detected at the element 48 and signal received from the monitor 58 to provide a train of signals that represent a line of the image obtained at the input face 30 of the image intensifier 32. This information can be displayed on a video display unit (VDU) 64.

The collimator 40 can be translated in the focused image plane 38 and so can pass succesive lines of the image produced at the output face 34 of the image intensifier 32 to the array 48. The microcomputer 56 can thus provide successive image lines to generate a two dimensional image on the VDU 64 of the artery 10.

The arrangement of the collimator 40 and the diode array 48 can best be seen in FIGS. 3 and 4. The slit 42 of the collimator 40 is defined between a pair of thin plates 66, 68 that are mounted on a vertical support frame 72. Plate 66 is rigidly attached to support 72. Plate 68 slides in a dove tail guide 109 in support 72. The space between the edges of plates 66 and 68 defines the slit 42. A stepping motor 86 is rigidly attached to the support 72 and has a threaded shaft 100 that mates with a boss 101 attached to plate 68. The width of the slit 42 is controlled with the stepping motor 86.

Support 72 slides on a dove tail grove 108 cut into backing member 112 that is normally stationary with respect to the optical systems 36 and 44 and has a rectangular hole 117 cut in the centre. Stepping motor 113 is rigidly attached to the backing member 112 and has a threaded shaft 114 that mates with a boss 115. The boss 115 is fixed to the support 72 by means of a pivot that allows a small amount of rotation about axes 116 perpendicular to the suppor 72. This has the purpose of accommodating a small amount of misalignment between the boss 115 and shaft 114. Rotation of the shaft 114 causes vertical displacement of the frame 72 and, by virtue of the connection with plates 66 and 68, bodily moves the slit 42 in the direction of the image plane.

The slit 42 permits a narrow illuminated field indicated at an FIG. 2 to pass through the collimator which after passing through the optical system 44 impinges as a line on the input face 46 of the diode array 48. The diode array is a commercial unit available from E. G. & G. Reticon of Sunnyvale, Calif. and identified as the S Series Solidstate Line Scanners. The array 48 comprises 1024 of the elements 50. Each of the elements has a greater height than width to provide an aspect ratio of approximately 100:1. Typically the elements 50 are set on 25 micron centers and have a height of 2.5 mm. The array 48 is provided with a self-scanning circuit so that the signal from each of the elements 50 may be read sequentially. Upon vertical movement of the slit 42 through the stepping motor 86 the location of the line on the input face 46 is moved vertically but because of the height of the elements 50, scanning of the array will again provide a line of information corresponding to a line of the image received at the input face of the image intensifier.

The processing of the pulse train received from the array and the signal received from the monitor 58 is shown in FIG. 5. Data from the ADC's 54 and 62 is processed by direct memory access controllers 100, 102 respectively. These access controllers are standard components available from Intel under code no. 8237 and are able to handle the data at high speed. The DMA 100 inputs data received from the diode array 48 into a static memory 104 through a data bus 105. The static memory is available from COMPUPRO of Haywood, Calif. and is identified under the trade mark RAM·22. Data from the monitor 58 is processed through DMA 102 and stored in a buffer memory 106.

The manipulation of data received from the array 48 and the monitor 58 and the display of the processed data on the VDU 64 is controlled by a CPU 108. The CPU 108 is a Z80 microprocessor that accesses both the static memory 104 and the buffer memory 106 through the data bus 105. The processed data is stored in the static memory 104 for subsequent display on the VDU 64. The data received from the monitor 58 allows the diode array data to be modified to compensate for variations in the intensity of the source 22. The data received by the DMA 102 and stored in buffer memory 106 is subtracted from the data received in DMA 100 so that the data used for display purposes is correlated to a constant datum. The microcomputor 50 may also generate a signal after one line of information is obtained to operate the stepping monotor 86 and move the collimator 40 by one increment.

The apparatus shown in FIGS. 2 through 5 can be used in a number of different ways. In the scanning mode illustrated in FIGS. 2 through 5, the artery is first made opaque to the x-ray beam 24 by injection of the radio opaque dye and irradiated by the source 22. A single line of information from the resultant visible image is isolated by the slit 42 in the collimator 40 and impinges upon the input face 46 of the array 48. Each of the elements 50 is scanned subsequetly so that a train of signals each representing the intensity of the image at the element 50 is transmitted to the microcomputer 56 which stores them in the static memory 104 as a first line of information for display on the VDU. At the same time the signal from monitor 58 is stored in the buffer memory 106. After the information for the first line has been received by the microcomputer 56, the stepping motor 86 is operated and the position of the slit 42 adjusted so that a new line of information in the image is isolated. This information is again processed through the microcomputer 56 and stored in the static memory 104 for subsequent display as a second line of information on the VDU. This sequence is repeated until the full width of the artery has been scanned.

The microprocessor 108 operates on the data in memories 104, 116 to correlate each line of the image to a certain datum and stores the resultant data for display in the VDU 64.

The image generated by the microcomputer 56 on the VDU is shown in FIG. 6. It can be seen that the image obtained is a broad horizontal band representing the passage 14 with a dark region in the area of the stenosis 18. This dark region is produced because the cross-sectional area of the passage 14 has been reduced and therefore the amount of X-rays absorbed in that region is less.

Represented below the image is a read out of the signals stored in the memory 104 for each of the diode elements 50 for one scan of the array 48. It will be seen that the signal is relatively uniform except in the area of the stenosis where there is a significant reduction in the signal level. By normalising and summing the signals in a line through a cross section of the arterial image the relative percentage of the stenosis can be calculated and thereby a quantitive value of the degree of stenosis can be obtained.

The apparatus shown in FIGS. 2 through 4 also permits the use of additional test techniques to obtain further information about the nature of the stenosis 18. FIG. 7 shows a schematic representation of the tests in which the artery 10 is injected with the radio-opaque dye and its progress through the artery monitered. To perform these tests the slit 42 is widened so that the whole of the image produced by the artery is received at the array 48. The computer 56 controls scanning of the array which commences just prior to the injection of the radio-opaque dye. The computer 56 may scan the array 48 and store data sufficiently quickly that progress of the dye along the artery may be observed. The information from successive scans is stored in the memory 104 and then displayed as successive lines on the VDU 64. In this way the vertical axis of the VDU is effectively a time axis and the progression of the leading edge of the radio-opaque dye along the artery can be observed.

For this test the amount of radio-opaque dye is reduced to a level that a slug of the dye will pass through the artery during the period of the test. During the first scan the leading edge of the dye is detected at the first of the arrays 50. On subsequent scans the leading edge of the dye will be detected at different elements 50 along the array 48. Because each subsequent scan is displaced on the vertical axis of the VDU 64 the image displayed is that seen of FIG. 8 which is an inclined line extending across the VDU screen. As the slug of dye passes through the artery, the first of the elements 50 will detect a loss of signal which will proceed along successive elements until the dye has passed through the area under investigation. Thus the line on the image will have a finite width and the slope of the line will give an indication of the mean flow velocity in the artery.

If the stenosis 18 is sufficiently severe to cause flow separation in the zones 20 the radio-opaque dye will be trapped in those zones after the main slug of the dye has passed through the artery. The trapped radio-opaque dye can be observed on the time position image of FIG. 8 as vertical white streaks which may therefor be used to provide an indication of the severity of the stenosis and the possibility of flow separation to one or both of sides of the stenosis 18.

The presence of a stenosis in the artery 10 may be detected on the time position curve by departure of the image of the arteries from a straight line. Thus, as shown in the example shown in FIG. 8, the gradient of the upper edge of the image increases adjacent position 5 to indicate an increase in the velocity of the blood in the artery and therefor a restriction in the cross sectional area of the artery.

Further information regarding the nature of the stenosis may be obtained by taking the readings of one element along the array and plotting it as dye concentration versus time. This plot is seen in FIG. 9 and is known as the Dilution Curve. Where the leading edge of the dye is detected, an almost vertical line results, as indicated at AB, within the progressive dilution of the dye in the artery being indicated by the generally exponential curve BC. Under ideal conditions, i.e. no stenosis in the artery, the time dilution curve for each of the element 50 would be similar. However, where the dye may be trapped, such as in the flow separation cells 20, the dilution curve will be identified as indicated in the chain dotted line on FIG. 9.

The presence of flow separation can therefor be detected by plotting the first moment of the area under the time dilution curve against position along the array. Such a plot is shown in FIG. 10 where different lines represent diferent degrees of stenosis. The generally upward slope of each of the lines may be attributed to the gradual spreading of the dye from its initial dimensions as it progresses along the artery. It will be seen that between 4 and 10% stenosis two peaks, F and G, are observed on the first moment axis. These peaks correspond to the location of the flow separation zone 20 along the artery and quite clearly indicate the onset of flow separation and the degree of separation in the stenosis. Thus by observing the first moment versus position plot as shown in FIG. 10 are indications of the degree of stenosis and the serverity of that stenosis may be obtained.

It will be observed therefore that the apparatus described in FIGS. 2 through 4 enable a number of different methods to be used to obtain information regarding the nature of the stenosis. Because of the high dynamic range of the array 48 the noise in the image is significantly reduced providing satisfactory image quality and the scanning speed of the array enables the time dimension to be investigated to provide additional information regarding the nature of the stenosis.

We claim:

1. Apparatus for monitoring the passage of radiopaque materials in a blood vessel comprising an x-ray source to irradiate said blood vessel, x-ray image collection means to receive an x-ray image including said blood vessel, conversion means to convert said x-ray image into a visible image, collimating means to select a discreet portion of said visible image and produce an elongate field of illumination representative of said blood vessel, a light detecting arrangement to receive said elongate field of illumination and having a plurality of discrete detectors spaced in a row along the axis of said elongate field, each having a length at least equal to the width of said elongate field to produce a signal upon impingement by said elongate field and scanning means to scan sequentially and exclusively said detectors and output said signals in series.

2. Apparatus according to claim 1 including means to store said signals.

3. Apparatus according to claim 2 including a monitor to monitor said source and provide a signal upon variation thereof from a predetermined level, said monitor signal modifying each of said signals to correlate said signals to a datum.

4. Apparatus according to claim 1 wherein said collimating means is movable in a direction transverse to said field of illumination to vary the portion of said image received by said arrangement.

5. Apparatus according to claim 2 including display means to display the signals stored on said storage means.

6. Apparatus according to claim 5 wherein said display means displays each series of signals as a line.

7. Apparatus according to claim 6 wherein each subsequent series of signals is displayed on said display means displaced from but generally parallel to the previous series of signals.

8. A method of investigating the presence of a stenosis in a blood vessel, comprising the steps of:
   interrogating a region of blood vessel by a beam of x-rays to form an x-ray image;
   converting the x-ray image so produced to a visible image including said region;
   isolating a portion of said visible image by collimating means to produce an elongate field representative of said region;
   aligning the axis of a light detecting arrangement with a predetermined cross-section of said elongate field, said light detecting arrangement having a plurality of detectors in series and centrally disposed about said axis, each of said detectors being sensitive to light emitted from a given area of said elongate field;
   injecting a radio opaque material into said blood vessel upstream of said region, and
   performing a first sequential scan of each detector to produce a train of signals indicative of the presence of said material at said cross-section after a first time increment, and immediately thereafter,
   performing a subsequent series of sequential scans over series of time increments to monitor the progress of said material relative to said cross-section.

9. A method according to claim 8 including the step of monitoring the x-ray source and modifying the signals in said train upon variations in the intensity of said source.

10. A method as defined in claim 8 further comprising the step of measuring a predetermined quantity of said radio opaque material for insertion into said vessel thereby enabling the identification of the leading edge of said material upon entry thereof in said region and the identification of the trailing edge of said material upon exit thereof from said region.

11. A method as defined in claim 10 further comprising the step of continuing said sequential scans following the identification of said trailing edge so as to identify the presence of residual material entrained in flow separation zones within said region.

12. A method for investigating the presence of stenosis in a blood vessel comprising the steps of:
   interrogating a region of a blood vessel by a beam of x-rays to form an x-ray image;
   converting the x-ray image so produced to a visible image including said region;
   isolating a portion of said visible image by collimating means to produce an elongate field representative of a portion of said region;
   aligning the axis of a light detecting arrangement with the axis of said elongate field, said light detecting arrangement having a plurality of detectors in series and centrally disposed about said axis, each of said detectors sensitive to light emitted from an area of said elongate field, said area including the longitudinal edges of said elongate field;
   inserting a radio opaque material into said vessel upstream of said region, and
   performing a first sequential scan of each detector to produce a train of signals indicative of the presence of said material in said region after a first time increment, and immediately thereafter,
   performing a successive series of sequential scans over a series of time increments to monitor the progress of said material through said region.

13. A method according to claim 12 including the step of displaying the image obtained from sequential scans as spaced lines on a display device.

14. A method according to claim 13 including the step of determining the mean residence time for said dye in a plurality of selected positions in said vessel and plotting said time versus position on said array to indicate abnormalities in said vessel.

15. A method according to claim 14 including the step of determining the first moment of the dilution curve at each position to indicate mean residence time.

* * * * *